United States Patent
Dyck et al.

(10) Patent No.: US 9,474,701 B2
(45) Date of Patent: Oct. 25, 2016

(54) ANTIMICROBIAL SOAPS CONTAINING CARVACROL AND METHODS OF USING SAME

(71) Applicant: Hydromer, Inc., Branchburg, NJ (US)

(72) Inventors: Manfred F. Dyck, Far Hills, NJ (US);
Silke von Dyck, Far Hills, NJ (US);
Eric Becktel, Bridgewater, NJ (US);
Irina Grigorian, Bridgewater, NJ (US)

(73) Assignee: HYDROMER, INC., Branchburg, NJ (US)

( * ) Notice: Subject to any disclaimer, the term of this patent is extended or adjusted under 35 U.S.C. 154(b) by 0 days.

(21) Appl. No.: 14/849,393

(22) Filed: Sep. 9, 2015

(65) Prior Publication Data
US 2016/0067159 A1 Mar. 10, 2016

Related U.S. Application Data

(60) Provisional application No. 62/048,100, filed on Sep. 9, 2014.

(51) Int. Cl.
| *A01N 31/14* | (2006.01) |
| *A61K 8/34* | (2006.01) |
| *A01N 31/08* | (2006.01) |
| *A61Q 19/10* | (2006.01) |
| *A61K 8/92* | (2006.01) |
| *A61K 8/46* | (2006.01) |
| *A01N 31/02* | (2006.01) |

(52) U.S. Cl.
CPC ............... *A61K 8/347* (2013.01); *A01N 31/02* (2013.01); *A01N 31/08* (2013.01); *A61K 8/34* (2013.01); *A61K 8/463* (2013.01); *A61K 8/922* (2013.01); *A61Q 19/10* (2013.01)

(58) Field of Classification Search
CPC ...................................................... A61K 8/347
USPC ........................................................ 514/731
See application file for complete search history.

(56) References Cited

U.S. PATENT DOCUMENTS

| 5,965,518 | A | 10/1999 | Nakatsu et al. |
| 6,107,261 | A | 8/2000 | Taylor et al. |
| 6,204,230 | B1 | 3/2001 | Taylor et al. |
| 6,329,331 | B1 | 12/2001 | Aronson et al. |
| 6,852,681 | B1 | 2/2005 | Kerschner et al. |
| 6,884,763 | B2 | 4/2005 | Willard et al. |
| 7,465,469 | B2 | 12/2008 | Ben-Yehoshua |
| 8,222,192 | B2 | 7/2012 | Eng |
| 2008/0118591 | A1 | 5/2008 | Natsch |
| 2010/0216892 | A1 | 8/2010 | Schmaus et al. |
| 2011/0189239 | A1 | 8/2011 | Mansouri |
| 2013/0053422 | A1 | 2/2013 | Edmonds et al. |

FOREIGN PATENT DOCUMENTS

WO 2010010320 A1 1/2010

*Primary Examiner* — Nizal Chandrakumar
(74) *Attorney, Agent, or Firm* — Hoffmann & Baron, LLP

(57) ABSTRACT

The present invention relates to antimicrobial formulations containing carvacrol and at least one of the following 2-phenoxyethanol, caprylyl glycol and hexylene glycol.

4 Claims, No Drawings

ANTIMICROBIAL SOAPS CONTAINING CARVACROL AND METHODS OF USING SAME

This application claims the benefit of U.S. Provisional Application No. 62/048,100, filed Sep. 9, 2014, which is incorporated herein by reference in its entirety.

BACKGROUND OF THE INVENTION

The usefulness of antimicrobial soap products has recently been under scrutiny. For example, it has been found that the antibacterial/antiviral efficacy of triclosan-based soaps against *E. coli*, or mixed bacterial/viral cultures, is much lower, if anything at all, than the efficacy of 70% ethanol or 10% bleach (Aiello et al., "Consumer antibacterial soaps: effective or just risky?" *Clin Infect Dis.* 2007, 45 Sup. 2:S137-47; Aiello et al., "Relationship between triclosan and susceptibilities of bacteria isolated from hands in the community," *Antimicrob Agent Chemother* 2004; 48:2973-9; Steinmann et al., "Comparison of virucidal activity of alcohol-based hand sanitizers versus antimicrobial hand soaps in vitro and in vivo," *J Hosp Infect.* 2012, 82(4):277-80). Moreover, by a recent statement of Colleen Roger, PhD, lead microbiologist at the FDA, the FDA raised the question about the efficacy of triclosan-based cosmetic and sanitizing products: "In fact, there currently is no evidence that over-the-counter (OTC) antibacterial soap products are any more effective in preventing illness than washing with plain water." Henceforth, manufacturers of antibacterial products like hand soap or body wash will be required to prove the efficacy of their products (announced by the FDA on Dec. 6, 2013).

Further, in order for triclosan to be even somewhat effective, at least twenty minutes of contact time with the surface being sanitized is required (Wisplinghoff et al., "Resistance to disinfectants in epidemiologically defined clinical isolates of *Acinetobacter baumannii*," *J Hosp Infect* 2007, 66(2):174-81). Otherwise, triclosan provides nearly zero efficacy. Clearly, washing hands for at least twenty minutes is impractical. And if triclosan is diluted with water, its efficacy is further reduced. Typically, soaps are diluted with water in order to have a foaming effect in the hand washing process.

Also, there are several known side effects of triclosan use. For example, triclosan is known to stimulate bacterial resistance to dangerous bacterial strains such as Methicillin-resistant *Staphylococcus aureus* (MRSA) or *P. aeroginosa* (Benerjee et al., "Comparative analysis of newly introduced disinfectants in hospitals in India: An important aspect of infection control policy," *International Journal of Infection Control*, 2013, 9, 2-5; Brenwald et al., "Triclosan resistance in methicillin-resistant *Staphylococus aureus* (MRSA)," *J. Hosp. Infect.* 2003, 55(2):141-4; Chuanchuen et al., "High-level triclosan resistance in *Pseudomonas aeruginosa* is solely a result of efflux," *Am. J. Infect. Control.*, 2003, 31(2):124-7; Fiss et al., "Formation of chloroform and other chlorinated byproducts by chlorination of triclosan-containing antibacterial products," *Environ. Sci. Technol.* 2007, 41(7):2387-94).

Furthermore, recent data show that triclosan is responsible for altering hormone regulation, weakening the immune system, unhealthy weight loss, uncontrolled cell growth and causing allergic sensitization in children (Cherednichenko et al., "Triclosan impairs excitation-contraction coupling and $Ca_2^+$ dynamics in striated muscle," *Proc Natl Acad Sci USA.* 2012, 109(35):14158-63; Bertelsen et al., "Triclosan exposure and allergic sensitization in Norwegian children," *Allergy* 2013, 68(1):84-91). Also detectable levels of triclosan have been found in blood, urine and breast milk (Allmur, Mats. "Triclosan in plasma and milk from Swedish nursing mothers and their exposure via personal care products," 2006. *Sci. Total Environ.*, 372, 1:87-93).

Benzalkonium chloride is another product found in some of hand soaps; it purports 99.9% bacterial kill. The compound is known as a common preservative, but has serious side effects. For example, enrichment of benzalkonium chloride gives rise to resistant bacterial species as well as conjunctive toxicity and immunoinflammatory reactions (Rasmussen et al., "Benzalkonium chloride and Glaukoma," *J. Ocul. Pharmacol. Ther.* 2013; Tandukar et al., "Long-term exposure to Benzalkonium Chloride disinfectant results in change of microbial community structure and increased antimicrobial resistance," 2013, *Envron. Sci. Technol.* 47(17):9730-8; Kuda et al., "Resistance to benzalkonium chloride of bacteria dried with food elements on stainless steel surface," 2008, *LWT-Food Sci Technol*, 41, 988-993).

There is clearly a need for an antimicrobial soap that is effective in killing microbes but does not have deleterious side effects.

SUMMARY OF THE INVENTION

In one aspect, the present invention provides an antimicrobial formulation comprising: (a) carvacrol; and (b) 2-phenoxyethanol, wherein the ratio of carvacrol to 2-phenoxythanol ranges from about 10:0.1 to about 10:2. Typically, the antimicrobial formulation further comprises tea tree oil and/or lemongrass oil. Typically, the antimicrobial formulation further comprises sodium dodecyl sulfate.

In one aspect, the present invention provides an antibacterial formulation comprising: (a) about 2% to about 10%, by weight, of a carvacrol; and (b) about 0.01% to about 1%, by weight, of 2-phenoxyethanol. Typically, the antimicrobial formulation further comprises tea tree oil and/or lemongrass oil. Typically, the antimicrobial formulation further comprises sodium dodecyl sulfate.

In one aspect, the present invention provides an antimicrobial formulation comprising: (a) carvacrol; and (b) a mixture of 2-phenoxyethanol, caprylyl glycol and hexylene glycol, wherein the ratio of carvacrol to a mixture 2-phenoxythanol/caprylyl glycol/hexylene glycol ranges from about 10:0.1 to about 10:5. Typically, the antimicrobial formulation further comprises tea tree oil and/or lemongrass oil. Typically, the antimicrobial formulation further comprises sodium dodecyl sulfate.

In one aspect, the present invention provides an antimicrobial formulation comprising: (a) carvacrol; (b) 2-phenoxyethanol; (c) caprylyl glycol; and (d) hexylene glycol, wherein the ratio of carvacrol to 2-phenoxythanol ranges from about 10:0.1 to about 10:2; wherein the ratio of carvacrol to caprylyl glycol ranges from about 10:0.1 to about 10:1; and wherein the ratio of carvacrol to hexylene glycol ranges from about 10:0.02 to about 10:0.4. Typically, the antimicrobial formulation further comprises tea tree oil and/or lemongrass oil. Typically, the antimicrobial formulation further comprises is sodium dodecyl sulfate.

In one aspect, the present invention provides an antimicrobial concentrate formulation comprising: (a) about 3% to about 10%, by weight, of a carvacrol; (b) about 0.01% to about 1%, by weight, of 2-phenoxyethanol; (c) about 0.02% to about 0.3%, by weight, of caprylyl glycol; and (d) about 0.01% to about 0.3%, by weight, of hexylene glycol. Typically, the antimicrobial formulation further comprises tea tree oil and/or lemongrass oil. Typically, the antimicrobial formulation further comprises sodium dodecyl sulfate.

In one aspect, the present invention provides an antimicrobial formulation comprising: (a) about 0.1% to about 15%, by weight, of a carvacrol; (b) about 0.002% to about 1%, by weight, of 2-phenoxyethanol; (c) about 0.001% to about 0.3%, by weight, of caprylyl glycol; (d) about 0.0006% to about 1%, by weight, of hexylene glycol; and (e) about 90-95%, by weight, of water. Typically, the antimicrobial formulation further comprises tea tree oil and/or lemongrass oil. Typically, the antimicrobial formulation further comprises sodium dodecyl sulfate.

Typically, the formulations of the present invention are provided in the form of hand soaps.

DETAILED DESCRIPTION OF THE INVENTION

The present invention provides soap formulations which combine high antimicrobial efficacy and safety. The formulations comprise synergistic combinations of certain natural essential oil(s) and conditioning agents. In some embodiments, the formulation also comprises moisturizing systems. The formulations are excellent replacements for currently commercially available hand soaps, e.g., triclosan and benzalkonium chloride based hand soaps.

It has surprisingly been discovered that at certain relative amounts of particular natural essential oil(s) and conditioning agents, the antimicrobial efficacy of the component parts of the formulations of the present invention are synergistically enhanced.

The formulations can be supplied in any form. For example, the formulations can be supplied as concentrated liquids or can be supplied diluted with water. The formulation can also be supplied as bar soaps, e.g., hand soap.

Throughout this specification, quantities are defined by ranges, and by lower and upper boundaries of ranges. Each lower boundary can be combined with each upper boundary to define a range. The lower and upper boundaries should each be taken as a separate element.

In one aspect of the present invention, the active components of the formulations include carvacrol combined with at least one of the following: 2-phenoxyethanol, caprylyl glycol and hexylene glycol.

In one embodiment, the antimicrobial formulation comprises: (a) carvacrol; and (b) 2-phenoxyethanol. The preferred relative weight percentage of carvacrol to 2-phenoxythanol ranges from about 10:0.1 to about 10:2. Examples of other lower boundaries of this range include 10:0.15; 10:1 and 10:1.2. Examples of other upper boundaries of this range include 10:1.5; 10:1.7 and 10:1.9. For instance, a preferred relative weight percentage of carvacrol to 2-phenoxythanol ranges from about 70:1.

In another embodiment, the antimicrobial formulation comprises: (a) about 2% to about 10%, by weight, of a carvacrol; and (b) about 0.01% to about 1%, by weight, of 2-phenoxyethanol.

In another embodiment, the antimicrobial formulation comprises: (a) carvacrol; and (b) a mixture of 2-phenoxyethanol, caprylyl glycol and hexylene glycol. The preferred relative weight percentage of carvacrol to the mixture ranges from about 10:0.1 to about 10:5. Examples of other lower boundaries of this range include 10:0.2; 10:0.4 and 10:0.7. Examples of other upper boundaries of this range include 10:2; 10:3 and 10:4.

In a further embodiment, the antimicrobial formulation comprises: (a) carvacrol; (b) 2-phenoxyethanol; (c) caprylyl glycol; and (d) hexylene glycol. The preferred relative weight percentage of carvacrol to 2-phenoxythanol ranges from about 10:0.1 to about 10:2. Examples of other lower boundaries of this range include 10:0.3; 10:0.6 and 10:1. Examples of other upper boundaries of this range include 10:1.5; 10:1.7 and 10:1.8. In other embodiments, the preferred relative weight percentage of carvacrol to 2-phenoxythanol ranges from about 100:1 to about 50:1, e.g., 70:1. The preferred relative weight percentage of carvacrol to caprylyl glycol ranges from about 10:0.1 to about 10:1. Examples of other lower boundaries of this range include 10:0.3; 10:0.4 and 10:0.5. Examples of other upper boundaries of this range include 10:0.6; 10:0.7 and 10:0.8. In other embodiments, the preferred relative weight percentage of carvacrol to caprylyl glycol ranges from about 200:1 to about 100:1, e.g., 106:1. The preferred relative weight percentage of carvacrol to hexylene glycol ranges from about 10:0.02 to about 10:0.4. Examples of other lower boundaries of this range include 10:0.05; 10:0.07 and 10:0.1. Examples of other upper boundaries of this range include 10:0.1; 10:0.2 and 10:0.3. In other embodiments, the preferred relative weight percentage of carvacrol to hexylene glycol ranges from about 350:1 to about 100:1, e.g., 318:1.

In another embodiment, the antimicrobial formulation in concentrate form comprises: (a) about 3% to about 10%, by weight, of a carvacrol; (b) about 0.01% to about 1%, by weight, of 2-phenoxyethanol; (c) about 0.02% to about 0.3%, by weight, of caprylyl glycol; and (d) about 0.01% to about 0.3%, by weight, of hexylene glycol.

In another embodiment, the antimicrobial formulation comprises: (a) about 0.1% to about 10% or 15%, by weight, of a carvacrol; (b) about 0.002% to about 1%, by weight, of 2-phenoxyethanol; (c) about 0.001% to about 0.3%, by weight, of caprylyl glycol; (d) about 0.0006% to about 1%, by weight, of hexylene glycol; and (e) about 90-95%, by weight, of water.

In another aspect, the active components of the formulations of the present invention include at least one oregano oil derivative combined with at least one of the following: 2-phenoxyethanol, caprylyl glycol and hexylene glycol.

In one embodiment, the antimicrobial formulation comprises: (a) at least one oregano oil derivative; and (b) 2-phenoxyethanol. The preferred relative weight percentage of the oregano oil derivative to 2-phenoxythanol ranges from about 10:0.1 to about 10:2. Examples of other lower boundaries of this range include 10:0.15; 10:1 and 10:1.2. Examples of other upper boundaries of this range include 10:1.5; 10:1.7 and 10:1.9. For instance, a preferred relative weight percentage of carvacrol to 2-phenoxythanol ranges from about 70:1.

In another embodiment, the antimicrobial formulation comprises: (a) about 2% to about 10%, by weight, of at least one oregano oil derivative; and (b) about 0.01% to about 1%, by weight, of 2-phenoxyethanol.

In another embodiment, the antimicrobial formulation comprises: (a) at least one oregano oil derivative; and (b) a mixture of 2-phenoxyethanol, caprylyl glycol and hexylene glycol. The preferred relative weight percentage of the oregano oil derivative to the mixture ranges from about 10:0.1 to about 10:5. Examples of other lower boundaries of this range include 10:0.2; 10:0.4 and 10:0.7. Examples of other upper boundaries of this range include 10:2; 10:3 and 10:4.

In a further embodiment, the antimicrobial formulation comprises: (a) at least one oregano oil derivative; (b) 2-phenoxyethanol; (c) caprylyl glycol; and (d) hexylene glycol. The preferred relative weight percentage of the oregano oil derivative to 2-phenoxythanol ranges from about 10:0.1 to about 10:2. Examples of other lower boundaries of this range include 10:0.3; 10:0.6 and 10:1. Examples of other upper boundaries of this range include 10:1.5; 10:1.7 and 10:1.8. In other embodiments, the preferred relative weight percentage of the oregano oil derivative to 2-phenoxythanol ranges from about 100:1 to about 50, e.g., 70:1. The preferred relative weight percentage of the oregano oil derivative to caprylyl glycol ranges from about 10:0.1 to about 10:1. Examples of other lower boundaries of this range include 10:0.3; 10:0.4 and 10:0.5. Examples of other upper boundaries of this range include 10:0.6; 10:0.7 and 10:0.8. In other embodiments, the preferred relative weight percentage of the oregano oil derivative to caprylyl glycol ranges from about 200:1 to about 100:1, e.g., 106:1. The preferred relative weight percentage of the oregano oil derivative to hexylene glycol ranges from about 10:0.02 to about 10:0.4. Examples of other lower boundaries of this range include 10:0.05; 10:0.07 and 10:0.1. Examples of other upper boundaries of this range include 10:0.1; 10:0.2 and 10:0.3. In other embodiments, the preferred relative weight percentage of the oregano oil derivative to hexylene glycol ranges from about 350:1 to about 100:1, e.g., 318:1.

In another embodiment, the antimicrobial formulation in concentrate form comprises: (a) about 3% to about 10%, by weight, of at least one oregano oil derivative; (b) about 0.01% to about 1%, by weight, of 2-phenoxyethanol; (c) about 0.02% to about 0.3%, by weight, of caprylyl glycol; and (d) about 0.01% to about 0.3%, by weight, of hexylene glycol.

In another embodiment, the antimicrobial formulation comprises: (a) about 0.1% to about 10%, by weight, of a at least one oregano oil derivative; or about 0.1% to about 15%, by weight, of a at least one oregano oil derivative; (b) about 0.002% to about 1%, by weight, of 2-phenoxyethanol; (c) about 0.001% to about 0.3%, by weight, of caprylyl glycol; (d) about 0.0006% to about 1%, by weight, of hexylene glycol; and (e) about 90-95%, by weight, of water.

Some examples of oregano oil derivatives include the following: thymol, limonene, pinene, ocimene, and caryophyllene.

In some embodiments, the formulations can further comprise other essential oils. Examples of such essential oils include tea tree oil (*melaleuca* oil), lemongrass oil (*Cymbopogon*) and white grapefruit oil (*Citrus Paradisi* peel oil).

In some embodiments, the formulations do not include a foaming agent. Examples of foaming agents include sodium laureth sulfate, or sodium lauryl ether sulfate (SLES), sodium lauryl sulfate (also known as sodium dodecyl sulfate or SDS) and ammonium lauryl sulfate (ALS).

In some other embodiments, the formulations further comprise about 0.1% to about 15%, by weight, of a surfactant selected from the group consisting of an anionic surfactant, a cationic surfactant, a nonionic surfactant, an ampholytic surfactant, and mixtures thereof. In the concentrate form, the formulation typically comprises about 0.5% to about 2%, by weight, of surfactant. In the diluted form, the formulation typically comprises about 1.5% to about 5%, by weight, of surfactant. A preferred example of a surfactant is sodium dodecyl sulfate.

In addition to the active components, the formulations can include other, non-toxic auxiliary agents, as long as such agents do not detract from the benefits provided by the present formulations. These agents can, for example, facilitate the delivery and/or stabilize the composition (e.g., cosmetic stabilizers) with respect to its shelf life or its actual applications. In the concentrate form, the formulations typically comprise about 20% to about 40%, by weight, of auxiliary agents. In the diluted form, the formulations typically comprise about 45% to about 55%, by weight, of auxiliary agents.

For example, these formulations can contain water-soluble skin conditioning or moisturizing agents that do not interfere with the synergistic antimicrobial properties of the compositions. Examples of these ingredients are glycerin; glycols; polyols, such as polyethylene glycol; lanolin; aloe vera, grapefruit seed extract, and vitamins, such as E, C and A. These agents serve to assist in soothing and retaining moisture on the skin. Examples of stabilizing agents (i.e., stabilizers) include cosmetic stabilizers; radical scavengers; antioxidants; and UV absorbers e.g., cinnamate derivatives, benzophenone derivatives, vitamins and the like.

Agents such as colorants, fragrances and insect repellants (e.g., citronella) may also be included in the formulation of the composition. Other examples of agents include preservatives, excipients, pH buffering agents, alcohols, chelating agents (e.g., EDTA), film-forming or barrier forming hydrophilic binder combinations (e.g. polyurethanes and polyvinyl pyrrolidone) or other therapeutics, and mixtures thereof.

In one embodiment, the formulation comprises active components, wherein the active components consist of: at least one oregano oil derivative and/or carvacrol combined with at least one of the following: 2-phenoxyethanol, caprylyl glycol and hexylene glycol.

In one embodiment, the formulation consists of: at least one oregano oil derivative and/or carvacrol combined with at least one of the following: 2-phenoxyethanol, caprylyl glycol and hexylene glycol, and an essential oil and/or auxiliary ingredient.

In one embodiment, the formulation consists essentially of the active components of: at least one oregano oil derivative and/or carvacrol combined with at least one of the following: 2-phenoxyethanol, caprylyl glycol and hexylene glycol. That is, any other ingredients that may materially affect the basic and novel characteristics of the active components of the invention are specifically excluded from the formulation. Any component which can potentially cause an undesirable effect/side effect may materially affect the basic and novel characteristics of the active components of the invention. Examples of undesirable effects/side effects include an allergic response, antimicrobial resistance, altered hormone regulation, and weakened immune system.

EXAMPLES

The following examples serve to provide further appreciation of the invention but are not meant in any way to restrict the effective scope of the invention.

| Hydromer Antiseptic Soap | | Percent | Manufacturer |
|---|---|---|---|
| NMP Free V-100 (2324-054) | | 0.8 | Hydromer |
| 2-phenoxy ethanol | 0.35→0.0028 | | |
| caprylyl glycol | 0.23 → 0.00184 | | |
| hexylene glycol | 0.08 → 0.00064 | | |
| Stabilizer 2250-58 | 0.34 → 0.0027 | | |
| K90 20 | 41.5 → 0.332 | | |
| Polyurethane Mix | 5.0 → 0.04 | | |
| Water | 47.5 → 0.38 | | |
| Sodium Lauryl Sulfate | | 2.0 | |
| Glycerine | | 1.0 | |
| Polymer 2000 | | 0.8 | |

-continued

| Hydromer Antiseptic Soap | Percent | Manufacturer |
|---|---|---|
| Xanthan Gum | 0.3 | |
| Sodium Methyl Cocoyl Taurate (SMT) | 0.25 | |
| Carvacrol | 0.2 | |
| Aloe | 0.2 | |
| Lemongrass Oil | 0.1 | |
| Deionized Water | 94.35 | |
| TOTAL | 100 | |

Hydromer Antiseptic Soap

Formula

| Water | 89.9 |
|---|---|
| Xantham Gum | 0.2 |
| NMP Free V100 | 4 |
| Lecithin Ultralec P | 0.1 |
| Carvacrol | 1 |
| Lemongrass oil | 0.8 |
| Polymer 2000 | 4 |
| Total % | 100% |

A Hydromer Antiseptic Soap sample was sent to EMSL Analytical, Inc., a high quality laboratory services company. The challenged bacteria in their study are commonly found in any bathrooms, i.e., *E. coli*, as well as antibiotic resistant strains, e.g., Methicillin-resistant *Staphylococcus aureus* (MRSA), Vancomycin-resistant enterococci (VRE), *C. difficile*, bacteria that causes extremely dangerous antibiotic resistant diarrhea, especially in hospitals, and Klibsiella Pneumonia. Hydromer Antiseptic Soap was tested in comparison with a commercially available triclosan-based antibacterial liquid soap. The efficacy of soap was measured as percent of bacterial reduction in a control sample after 30 sec of a contact time with soaps.

The conclusions provided by EMSL Analytical, Inc. stated that Hydromer Antiseptic Soap has strong antimicrobial efficacy. After 30 sec of exposure time, the Hydromer Antiseptic Soap significantly (up to 99.95%) reduced all of the bacteria tested. There were no viable bacteria detected in a control sample after a 30 sec exposure to the Hydromer Antiseptic Soap with a detection limit of 10 Colony Forming Unit per ml. The triclosan based antibacterial soap did not show any visible antimicrobial effectiveness at 30 seconds of exposure under established testing protocol. (EMSL final report, 02/19/2014/order N151400397). In contrast, the chemistry of essential oils used in the formulation of Hydromer Antiseptic Soap provided effective inhibition of pathogenic bacteria without any dermatological side effects (Bart, S. "Essential oils: their antibacterial properties and potential applications in food," 2004, *Int. J. Food Microbil.*, 94, 223-253).

Challenge Bacteria: Methicillin-Resistant *Staphylococcus aureus* (MRSA), ATCC 33592
*Escherichia coli*, ATCC 25922
Vancomycin-Resistant *Enterococcus* (VRE), ATCC 51299
*Klebsiella pneumoniae*, ATCC 35651
*Clostridium difficile* (C. diff), ATCC 70057
*Norovirus* spp.
*Salmonella* spp.
*Campylobacter* spp.

Experimental Summary:

The testing procedure was designed after discussions between EMSL Analytical, the testing company, and the client, Hydromer, Inc. The client provided a protocol for Antiseptic Soap testing in a reference publication from the University of Kansas. The testing was conducted in a Houston Microbiology Laboratory.

Procedure:

Two kinds of hand soaps were tested at a 1:10 dilution with sterile tap water: Hydromer Antiseptic Soap 2319-115D and a Triclosan Based Antibacterial Soap. Pure cultures of each bacterium were grown on Tryptic soy agar (TSA) plates and incubated at 37° C. for 24 hours. C. diff was grown under anaerobic conditions. Pure isolates were harvested and individually suspended into Tryptic soy broth (TSB) to produce culture solutions for testing.

The testing was performed in 1.5 mL tubes. In each tube, 0.1 mL of culture solution was added into 0.9 mL of the hand soap. After 30 seconds of contact time, the tubes were centrifuged at high speed (~4000 rpm) for 5 minutes to separate the culture from the solution. The supernatant was discarded and the tube refilled with sterile deionized water and vortexed to resuspend any recovered bacteria. This solution was spread plated onto TSA at multiple dilutions and incubated for 24 hrs at 37° C. for 24 hours. All soap tests were performed in triplicate. Controls were performed in duplicate with untreated bacteria.

Experimental Results:

TABLE 1.1

Hand soap effectiveness against VRE.

| Sample | Exposure Time | Avg CFU (per mL) | Avg Log10/CFU | Log Reduction | % Reduction |
|---|---|---|---|---|---|
| Control | 30 sec | >30,000 | 4.48 | | |
| Triclosan Hand Soap | 30 sec | >30,000 | 4.48 | 0.00 | <1.00 |
| Hydromer Antiseptic Soap | 30 sec | <10 | 1.00 | 3.48 | >99.97 |

Log Reduction = difference between Log Control and test soap after 30 seconds exposure.
Detection limit: 10 CFU/mL

TABLE 1.2

Hand soap effectiveness against MRSA.

| Sample | Exposure Time | Avg CFU (per mL) | Avg Log10/CFU | Log Reduction | % Reduction |
|---|---|---|---|---|---|
| Control | 30 sec | >30,000 | 4.48 | | |
| Triclosan Hand Soap | 30 sec | >30,000 | 4.48 | 0.00 | <1.00 |
| Hydromer Antiseptic Soap | 30 sec | <10 | 1.00 | 3.48 | >99.97 |

Log Reduction = difference between Log Control and test soap after 30 seconds exposure.
Detection limit: 10 CFU/mL

TABLE 1.3

Hand soap effectiveness against *E. coli*.

| Sample | Exposure Time | Avg CFU (per mL) | Avg Log10/CFU | Log Reduction | % Reduction |
|---|---|---|---|---|---|
| Control | 30 sec | 239,000 | 4.36 | | |
| Triclosan Hand Soap | 30 sec | >300,000 | 4.48 | −0.11 | <1.00 |
| Hydromer Antiseptic Soap | 30 sec | <10 | 1.00 | 3.36 | 99.96 |

Log Reduction = difference between Log Control and test soap after 30 seconds exposure.
Detection limit: 10 CFU/mL

TABLE 1.4

Hand soap effectiveness against *Klebsiella pneumoniae*.

| Sample | Exposure Time | Avg CFU (per mL) | Avg Log10/CFU | Log Reduction | % Reduction |
|---|---|---|---|---|---|
| Control | 30 sec | 209,000 | 4.27 | | |
| Triclosan Hand Soap | 30 sec | >300,000 | 4.48 | −0.20 | <1.00 |
| Hydromer Antiseptic Soap | 30 sec | <10 | 1.00 | 3.27 | 99.95 |

Log Reduction = difference between Log Control and test soap after 30 seconds exposure.
Detection limit: 10 CFU/mL

TABLE 1.5

Hand soap effectiveness against *C. diff*.

| Sample | Exposure Time | Avg CFU (per mL) | Avg Log10/CFU | Log Reduction | % Reduction |
|---|---|---|---|---|---|
| Control | 30 sec | 485 | 2.59 | | |
| Triclosan Hand Soap | 30 sec | 373 | 2.57 | 0.02 | 4.11 |
| Hydromer Antiseptic Soap | 30 sec | <10 | 1.00 | 1.59 | 97.4 |

Log Reduction = difference between Log Control and test soap after 30 seconds exposure.
Detection limit: 10 CFU/mL

TABLE 2

Control Blank results.

| Blank | Growth/No Growth |
|---|---|
| Dilution water | No Growth |
| Hydromer Antiseptic Soap | No Growth |
| Triclosan | No Growth |

Conclusions/Observations:

The Hydromer Antiseptic Soap had strong antimicrobial effectiveness. After 30 seconds of exposure time, the Hydromer Antiseptic Soap significantly reduced all the bacteria tested. There were no viable bacteria detected after exposure to the Hydromer Antiseptic Soap with a detection limit of 10 CFU per mL. The triclosan based hand soap did not show antimicrobial effectiveness at 30 seconds of exposure under this testing protocol.

Synergistic Effect of Hydromer Antiseptic Soap Ingredients

Objectives:

Main ingredients of NMP free V100, (2-Phenoxyethanol, Caprylyl glycol and Hexylene Glycol) were analyzed with/without Carvacrol.

| Formulations checked % | Efficacy against gram negative/gram positive bacteria | Synergistic effect |
|---|---|---|
| Analysis of the NMP free V100 synergism with the Carvacrol | | |
| 4% NMP free V100 | No Inhibition | n/a |
| 0.2% Carvacrol | NO Inhibition | n/a |
| 0.2% Carvacrol + 4% NMP free V100 | 90% Bacterial Growth Inhibition | Strong synergistic effect |
| Analysis of the main ingredients of V100 synergism with the Carvacrol | | |
| 0.035% 2-Phenoxyethanol | NO Inhibition | n/a |
| 0.2% Carvacrol + 0.035% 2-Phenoxyethanol | 90% Bacterial Growth Inhibition | Strong synergistic effect |
| 0.02% Caprylyl Glycol | NO Inhibition | n/a |
| 0.2% Carvacrol + 0.02% Caprylyl Glycol | 80% Bacterial Growth Inhibition | Strong synergistic effect |
| 0.008% Hexylene Glycol | NO Inhibition | n/a |
| 0.2% Carvacrol + 0.008% Hexylene Glycol | 50% Bacterial Growth Inhibition | Mild synergistic effect |

Conclusion:

2 phenoxyethanol and Caprylyl Glycol act synergistically with carvacrol in a formulation of the present invention.

Synergistic Effect of Hydromer Antismicrobial Soap Ingredients

Objectives:

Main ingredients of NMP free V100, 2-Phenoxyethanol, Caprylyl glycol and Hexylene Glycol were analyzed in the concentrations that they appear in the Hydromer Antiseptic Soap with/without Oregano Oil.

| Formulations checked % | Efficacy against gram negative/gram positive bacteria | Synergistic effect |
|---|---|---|
| 4% NMP free V100 | No Inhibition | n/a |
| 0.2% Oregano Oil | Below 50% Inhibition | n/a |
| 0.2% Oregano Oil + 4% NMP free V100 | 90% Inhibition | Strong synergistic effect |
| Update Apr. 28, 2014 | | |
| 0.035% 2-Phenoxyethanol | NO Inhibition | n/a |
| 0.2% Oregano Oil + 0.035% 2-Phenoxyethanol | 90% Inhibition | Strong synergistic effect |
| 0.02% Caprylyl Glycol | NO Inhibition | n/a |
| 0.2% Oregano Oil + 0.02% Caprylyl Glycol | 80% Inhibition | Strong synergistic effect |
| 0.008% Hexylene Glycol | NO Inhibition | n/a |
| 0.2% Oregano Oil + 0.008% Hexylene Glycol | 50% Inhibition | Mild synergistic effect |

Conclusion:

2 phenoxyethanol and Caprylyl Glycol act synergistically with the Oregano Oil in the formulation of Hydromer Antimicrobial Soap.

| Microorganism | Hydromer Antiseptic Soap | References |
|---|---|---|
| *Escherichia coli* | >99.97% reduction at 30 sec contact time | EMSL Analytical Inc. N151400397 Feb. 19, 2014 |
| Methicillin-resistant *Staphylococcus aureus* (MRSA) | >99.97% reduction at 30 sec contact time | EMSL Analytical Inc. N151400397 Feb. 19, 2014 |
| Vancomycin-resistant *Enterococcus* (VRE) | >99.97% reduction at 30 sec contact time | EMSL Analytical Inc. N151400397 Feb. 19, 2014 |
| *Klebsiella pneumoniae* | >99.97% reduction at 30 sec contact time | EMSL Analytical Inc. N151400397 Feb. 19, 2014 |
| *Salmonella enterica* | >99.97% reduction at 30 sec contact time | EMSL Analytical Inc. N151406704 Jan. 08, 2015 |
| *Campylobacter Jejuni* | >99.97% reduction at 30 sec contact time | EMSL Analytical Inc. N151406704 Jan. 08, 2015 |
| *Feline calcivirus* ATCC VR 782-US EPA-approved surrogate microorganism for Human Norovirus Label claims | >99.97% reduction at 30 sec contact time | Antimicrobial Test Laboratories/NG6063-A1 15 May 2015 |

EMSL Final Report. Determining the Activity of Antimicrobial Hand Soap. February 2014. Order N 151400397.

The invention claimed is:

1. An antimicrobial formulation comprising:
   (a) carvacrol;
   (b) 2-phenoxyethanol;
   (c) caprylyl glycol; and
   (d) hexylene glycol,
wherein the ratio of carvacrol to 2-phenoxythanol ranges from about 10:0.1 to about 10:2;
wherein the ratio of carvacrol to caprylyl glycol ranges from about 10:0.1 to about 10:1; and
wherein the ratio of carvacrol to hexylene glycol ranges from about 10:0.02 to about 10:0.4.

2. The antimicrobial formulation of claim 1 further comprising tea tree oil and/or lemongrass oil.

3. The antimicrobial formulation of claim 1 further comprising is sodium dodecyl sulfate.

4. The antimicrobial formulation of claim 1 in the form of hand soap.

* * * * *